United States Patent
Lee et al.

(10) Patent No.: US 8,097,726 B2
(45) Date of Patent: Jan. 17, 2012

(54) HUPERZINE A COMPOUND FOR TREATMENT OF ALZHEIMER'S DISEASE

(75) Inventors: On Lee, Hsinchu (TW); Jenn-Tsang Hwang, Hsinchu (TW); Chi-Y Hung, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 989 days.

(21) Appl. No.: 11/798,886

(22) Filed: May 17, 2007

(65) Prior Publication Data

US 2007/0270454 A1    Nov. 22, 2007

Related U.S. Application Data

(60) Provisional application No. 60/800,859, filed on May 17, 2006.

(51) Int. Cl.
*C07D 221/22* (2006.01)
*A61K 31/439* (2006.01)

(52) U.S. Cl. .......................... 546/97; 514/290
(58) Field of Classification Search ............ 546/97
See application file for complete search history.

(56) References Cited

U.S. PATENT DOCUMENTS

| | | | |
|---|---|---|---|
| 4,929,731 A | 5/1990 | Kozikowski et al. |
| 5,104,880 A | 4/1992 | Kozikowski |
| 5,106,979 A | 4/1992 | Kozikowski et al. |
| 5,177,082 A | 1/1993 | Yu et al. |
| 5,547,960 A | 8/1996 | Kozikowski et al. |
| 5,663,344 A | 9/1997 | Kozikowski et al. |
| 5,869,672 A | 2/1999 | Kozikowski et al. |
| 5,929,084 A | 7/1999 | Zhu et al. |
| RE38,460 E | 3/2004 | Zhu et al. |

FOREIGN PATENT DOCUMENTS

| | | | |
|---|---|---|---|
| WO | WO 9620176 | * | 7/1996 |
| WO | WO-99/11625 A1 | | 3/1999 |
| WO | WO 9911625 | * | 3/1999 |
| WO | WO-2007/014498 A1 | | 2/2007 |

OTHER PUBLICATIONS

Dorwald F. A. Side Reactions in Organic Synthesis, 2005, Wiley: VCH, Weinheim p. IX of Preface.*
Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed "., Marcel Dekker, New York, 1996, pp. 451 and 596.*
Anthony West, West, Anthony R., Solid State Chemistry and its Applications, Wiley, New York, 1988, pp. 358 & 365.*
Taiwanese Office Action dated Sep. 6, 2010 for Application No. 096117552.

* cited by examiner

*Primary Examiner* — Rita Desai
(74) *Attorney, Agent, or Firm* — Birch, Stewart, Kolasch & Birch, LLP

(57) ABSTRACT

A huperzine A compound is provided. The huperzine A compound has following formula:

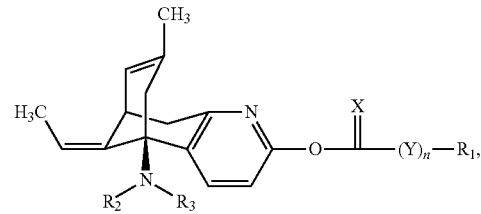

wherein X comprises O or S, Y comprises —O—, —S—, —CH($R_4$)—, —C($R_4$)($R_5$)—, —C($R_4$)=C($R_5$)—, —C≡C—, —NH— or —N($R_4$)—, n is 0, 1 or 2, $R_3$ is C(=X)—(Y)$_n$—$R_1$ provided that $R_2$ is H or $R_2$ and $R_3$ are combined to form =CH—Ar, wherein $R_1$, $R_4$ and $R_5$ independently comprise hydrogen, $C_1$-$C_{32}$ alkyl, $C_1$-$C_{32}$ alkenyl, $C_1$-$C_{32}$ alkynyl, $C_1$-$C_{32}$ aryl or $C_1$-$C_{32}$ heteroaryl, in which alkyl, alkenyl, alkynyl, aryl or heteroaryl with one or more substituents comprising halogen, hydroxyl, alkoxy, aryloxyl, amino, alkylamino, arylamino, dialkylamino, diarylamino, imino, alkylimino, arylimino, acylamido, diacylamido, acylimido, cyano, nitro, mercapto, carbamido, carbamoyl, carboxyl, thioureido, thiocyanato, sulfonamido, thio, sulfonyl or sulfinyl, and Ar comprises aryl or heteroaryl.

16 Claims, No Drawings

HUPERZINE A COMPOUND FOR TREATMENT OF ALZHEIMER'S DISEASE

This Nonprovisional application claims priority under 35 U.S.C. §119(e) on U.S. Provisional Application Nos. 60/800, 859 filed on May 17, 2006 the entire contents of which are hereby incorporated by reference.

BACKGROUND OF THE INVENTION

1. Field of the Invention

The invention relates to a medicine, and in particular to a huperzine A compound used in the treatment of Alzheimer's disease.

2. Description of the Related Art

Alzheimer's disease (AD) accounts for about 75% of aged dementia. This central nervous system disorder is marked by a variety of symptoms such as degeneration of neurons, development of amyloid plaque, neurofibrillary tangle, and declination of acetylcholine and atrophy of cerebral cortex. Patients with AD initially suffer from short-term memory loss, followed by a drop in cognitive function and finally, lose the ability to care for themselves.

AD affects about 10% of the population beyond age 65. It attacks 19% of individuals 75 to 85 years old, and 45% over age 85. AD is the fourth leading cause of death in adults, behind heart disease, cancer, and stroke. The cost of caring for patients, including diagnosis, nursing, at-home care, and lost wages combined, is estimated to be 40 to 90 billion US dollars per year.

Although there has been great progress in understanding the pathophysiologic mechanisms of the disease, the causes of AD are still poorly understood. Possible causes include genetic predisposition, neurotransmitter defects, inflammation, metabolic decline, oxidative stress, and excitatory amino acid toxicity; none of these causes however, is alone conclusive.

Several compounds are currently used in clinical practice for the treatment of AD according to the current understanding of its pathogenesis. Among these drugs, notable are acetylcholine esterase (AchE) inhibitors. AchE inhibitors, such as donepezil, rivastigmine, tacrine, galantamine and huperzine A (huperzine A) all have received regulatory approval for AD treatment in a variety of countries.

Huperzine A is an alkaloid isolated from Lycopodium serratum, a Chinese traditional medicinal herb. Huperzine A appears to be more specific and potent in inhibiting AchE compared to tacrine and donepezil as demonstrated in both in vitro and in animal models. The three-dimensional crystal structure of the AchE/huperzine A complex shows a strong hydrophobic interaction between huperzine A and the active-site pocket of AchE. Further studies have revealed that huperzine A is capable of penetrating the blood-brain barrier to produce a dose-dependent increase of Ach, norepinephrine, and dopamine in rat cortex by systemic or local administration of huperzine A. It also appears that huperzine A demonstrates promising effects in protecting neurons from neurotoxins. Evidence obtained from studies employing rat embryo hippocampus and cerebellum cultured cells have revealed that huperzine A decreases the death of neuronal cell caused by toxic levels of glutamate. The pharmacokinetic evaluation of a single oral dose of huperzine A to volunteers showed that huperzine A was absorbed rapidly, distributed widely in the body, and eliminated at a moderate rate. In a small double blind clinical study conducted in China, huperzine A administered orally at 0.2 mg twice a day for 8 weeks had demonstrated significant improvement in memory, cognition and behavior in 58% patients without causing any severe side effects to the volunteers.

Because huperzine A is rapidly eliminated from the kidneys, its half-life in plasma is only 4 to 5 hours. Thus, the clinical oral dosage of huperzine A for treatment of Alzheimer's disease varies from 5 to 20 mg with a dose frequency of 2-4 times per day. One important concern in the administration of drugs for AD is convenience of self-medication for patients as well as caregivers, particularly elderly patients suffering from dementia or memory disorders. Repeated administration of drugs may be troublesome with these patients as they tend to forget to take the medication at the scheduled time or otherwise may require a caregiver to ensure the medication schedule is maintained. Thus, means for achievements of conveniently administration of drug and keeping medication at the scheduled time, administration of huperzine A to AD patients once-daily is highly desirable.

Another important factor in determining whether AD patients maintain medication schedules is drug adverse reactions. Available data indicate that the adverse effects of huperzine A at therapeutic dosages are primarily cholinergic and include nausea, vomiting, diarrhea, hyperactivity, dizziness, and anorexia. Clinically important bradycardia was also noted in one clinical study and may form a problem for patients with existing cardiac disease. The causes of these adverse effects may be due to the excellent absorption and wide distribution of huperzine A as well as rapid penetration into the brain to produce a rapid increased acetylcholine level. Thus, a means for controlled exposure of huperzine A to AD patients capable of reducing adverse effects is highly desirable.

Several conventional huperzine A compounds, their structures and applications thereof have been disclosed, for example, by U.S. Pat. No. 4,929,731, U.S. Pat. No. 5,104,880, U.S. Pat. No. 5,106,979, U.S. Pat. No. 5,177,082, U.S. Pat. No. 5,547,960, U.S. Pat. No. 5,663,344, U.S. Pat. No. 5,869,672, U.S. Pat. No. 5,929,084, U.S. Pat. No. RE38460, WO 99/11625 and WO 2007/014498.

BRIEF SUMMARY OF THE INVENTION

An embodiment of the invention provides a huperzine A compound having the structure:

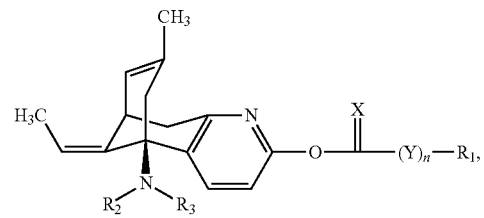

wherein X comprises O or S; Y comprises —O—, —S—, —CH($R_4$)—, —C($R_4$)($R_5$)—, —C($R_4$)=C($R_5$)—, —C≡C—, —NH— or —N($R_4$)—; n is 0, 1 or 2; $R_3$ is C(=X)—(Y)$_n$—$R_1$ provided that $R_2$ is H or $R_2$ and $R_3$ are combined to form =CH—Ar, wherein $R_1$, $R_4$ and $R_5$ independently comprise hydrogen, $C_1$-$C_{32}$ alkyl, $C_1$-$C_{32}$ alkenyl, $C_1$-$C_{32}$ alkynyl, $C_1$-$C_{32}$ aryl or $C_1$-$C_{32}$ heteroaryl, in which alkyl, alkenyl, alkynyl, aryl or heteroaryl with one or more substituents comprising halogen, hydroxyl, alkoxy, aryloxyl, amino, alkylamino, arylamino, dialkylamino, diarylamino, imino, alkylimino, arylimino, acylamido, diacylamido, acylimido, cyano, nitro, mercapto, carbamido, carbamoyl, carboxyl, thioureido, thiocyanato, sulfonamido, thio, sulfonyl or sulfinyl, and Ar comprises aryl or heteroaryl, in which with one or more substituents comprising halogen, hydroxyl, alkoxy, aryloxyl, amino, alkylamino, arylamino, dialkylamino, diarylamino, imino, alkylimino, arylimino, acylamido, diacylamido, acylimido, cyano, nitro, mercapto, carbamido, carbamoyl, carboxyl, thioureido, thiocyanato, sulfonamido, thio, sulfonyl or sulfinyl.

An embodiment of the invention provides a pharmaceutical composition comprising the disclosed huperzine A compound and a pharmaceutically acceptable salts, complexes or solvates.

An embodiment of the invention provides a method of treating dysmnesia caused by a failure in central cholinergic system by inhibiting cholinesterase comprising administering the disclosed huperzine A compound to a patient in an effective amount.

An embodiment of the invention provides a method of treating myasthenia by inhibiting cholinesterase comprising administering the disclosed huperzine A compound to a patient in an effective amount.

An embodiment of the invention provides a method of inhibiting cholinesterase comprising administering the disclosed huperzine A compound to a patient in an effective amount.

An embodiment of the invention also provides a method of improving memory impairment comprising administering the disclosed huperzine A compound to a patient in an effective amount.

An embodiment of the invention further provides a method of detoxification comprising administering the huperzine A compound in an effective amount to block binding of toxicant to cholinesterase.

A detailed description of the invention is provided in the following.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

An embodiment of the invention provides a huperzine A compound having the structure:

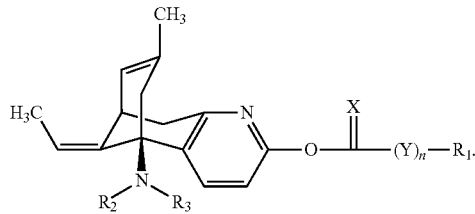

In the preceding structure, X may comprise O or S.

Y may comprise —O—, —S—, —CH($R_4$)—, —C($R_4$)($R_5$)—, —C($R_4$)=($R_5$)—, —C≡C—, —NH— or —N($R_4$)—. $R_4$ and $R_5$ may independently comprise hydrogen, $C_1$-$C_{32}$ alkyl, $C_1$-$C_{32}$ alkenyl, $C_1$-$C_{32}$ alkynyl, $C_1$-$C_{32}$ aryl or $C_1$-$C_{32}$ heteroaryl, in which alkyl, alkenyl, alkynyl, aryl or heteroaryl with one or more substituents such as halogen, hydroxyl, alkoxy, aryloxyl, amino, alkylamino, arylamino, dialkylamino, diarylamino, imino, alkylimino, arylimino, acylamido, diacylamido, acylimido, cyano, nitro, mercapto, carbamido, carbamoyl, carboxyl, thioureido, thiocyanato, sulfonamido, thio, sulfonyl or sulfinyl.

n may be 0, 1 or 2.

$R_3$ may be C(=X)—(Y)$_n$—$R_1$ provided that $R_2$ is H or $R_2$ and $R_3$ may be combined to form =CH—Ar. $R_1$ may comprise hydrogen, $C_1$-$C_{32}$ alkyl, $C_1$-$C_{32}$ alkenyl, $C_1$-$C_{32}$ alkynyl, $C_1$-$C_{32}$ aryl or $C_1$-$C_{32}$ heteroaryl, in which alkyl, alkenyl, alkynyl, aryl or heteroaryl with one or more substituents such as halogen, hydroxyl, alkoxy, aryloxyl, amino, alkylamino, arylamino, dialkylamino, diarylamino, imino, alkylimino, arylimino, acylamido, diacylamido, acylimido, cyano, nitro, mercapto, carbamido, carbamoyl, carboxyl, thioureido, thiocyanato, sulfonamido, thio, sulfonyl or sulfinyl. Ar may be aryl or heteroaryl, in which with one or more substituents such as halogen, hydroxyl, alkoxy, aryloxyl, amino, alkylamino, arylamino, dialkylamino, diarylamino, imino, alkylimino, arylimino, acylamido, diacylamido, acylimido, cyano, nitro, mercapto, carbamido, carbamoyl, carboxyl, thioureido, thiocyanato, sulfonamido, thio, sulfonyl or sulfinyl.

In the preceding embodiment of the invention, pharmaceutically acceptable salts thereof are also included. Any pharmaceutically acceptable salts now known, or to be developed, can be utilized and include, but are not limited to, those derived from inorganic acids such as hydrochloric, hydrobromic, sulfuric, sulfamic, phosphoric, carbonic, nitric and the like, and those prepared from organic acids such as acetic, propionic, succinic, glycolic, stearic, lactic, malic, tartaric, citric, ascorbic, pamoic, maleic, hydroxymaleic, phenylacetic, glutarnic, benzoic, salicylic, sulfanilic, 2-acetoxybenzoic, fumaric, toluenesulfonic, methanesulfonic, ethanedisulfonic, oxalic, isethionic, trifluoroacetic, gluconic and the like. Such salts can be prepared by methods commonly known to those skilled in the art.

In the preceding embodiment of the invention, pharmaceutically acceptable complexes thereof are also included. Any pharmaceutically acceptable complexes now known, or to be developed, can be utilized and include, but are not limited to, those derived from metal anions such as lithium, sodium, potassium, magnesium, calcium, aluminum, scandium, titanium, nickel, cobalt, iron, rare earth metal and the like, and those prepared from organic compounds such as cyclodextrins, calixirenes and the like. Such complexes can be prepared by methods commonly known to those skilled in the art.

In the preceding embodiment of the invention, pharmaceutically acceptable solvates thereof are also included. Any pharmaceutically acceptable solvates now known, or to be developed, can be utilized and include, but are not limited to, those derived from water, methanol, ethanol, propanol, ethyl acetate, dimethylformamide, diethylformamide, N-methylpyrrolidone, dimethylsulfoxide, sulfolene, tetrahydrofuran, acetone, methyl ethyl ketone, cyclohexanone, toluene, xylenes and the like. Such solvates can be prepared by methods commonly known to those skilled in the art.

It is to be understood that the compounds of the aforementioned formula can exist in racemic, i.e., (±)-form, or in the form of optical isomers, i.e., in the (±)- or (−)-form.

Without being limited by any particular theory, it is believed that the compounds in an embodiment of the invention may accumulate in "pool" sites of body, i.e., fatty domains of the brain, liver, lung, kidney or fatty tissue or albumin of plasma. In such pool sites, the compounds of the invention inhibit AChE, and treat AChE related disorders, such as dementia, myasthenia, age-related memory impairment, Down's syndrome and glaucoma.

In addition, it is believed that within the pool sites, the compounds of this invention slowly hydrolyze in the presence of esterases or other metabolic enzymes to provide huperzine A, which is capable of inhibiting AChE and treating AChE related disorders, such as dementia, myasthenia, age-related memory impairment, Down's syndrome and glaucoma. Thus, it is believed that the compounds of the invention in all its embodiments behave as prodrugs of huperzine A. As used in this description, prodrug refers to a derivative of huperzine A which, when administered to a mammal, especially a human, is hydrolyzed by esterases or other hydrolytic or metabolic enzymes endemic to brain, liver, kidney, plasma or other tissue, so as to cause huperzine A to be available at its target sites. The slow hydrolysis of the compounds in all embodiments of the invention is believed to provide a preferable slow release of huperzine A from the compounds thereof.

Unlike huperzine A, which is only slightly metabolized by mammals, and excreted without production of active metabolites, the compounds in all embodiments of the invention are believed to remain in circulation in the body and reside in any pool sites for relatively longer periods of time until they are hydrolyzed by the described enzymes to release the huperzine A for treating AChE related disorders.

An embodiment of the invention provides a method of treating myasthenia by inhibiting cholinesterase comprising administering the disclosed huperzine A compound to a patient in an effective amount.

An embodiment of the invention provides a method of treating dysmnesia caused by a failure in central cholinergic system by inhibiting cholinesterase comprising administering the disclosed huperzine A compound to a patient in an effective amount.

An embodiment of the invention also provides a method of improving memory impairment comprising administering the disclosed huperzine A compound to a patient in an effective amount.

An embodiment of the invention provides a method of inhibiting cholinesterase comprising administering the disclosed huperzine A compound to a patient in an effective amount.

An embodiment of the invention further provides a method of detoxification comprising administering the huperzine A compound in an effective amount to block binding of toxicant to cholinesterase.

The compounds in all embodiments of the invention are suitable for once-daily administration to provide therapeutic benefits to patients with Alzheimer disease. Further, the drug is smoothly released to prevent surges in plasma and brain, thus decreasing incidence of adverse effects in Alzheimer's patients.

The compounds in an embodiment of the invention are labile in acidic conditions such as gastric juice, weak basic condition such as intestinal juice or circulated blood, or prone to hydrolysis under the action of enzymes such as esterase, lipase, peptidase, amidase or pepsin. The aforementioned enzymes can be found in the gastrointestinal tract, liver, circulated blood or even the central nervous system. The adequate exposure of AD patients to huperzine A is achieved by spontaneous hydrolysis or enzymatic decomposition of the novel prodrug of the invention in a controlled manner. The hydrolysis rate of the novel prodrug of the invention can be fine tuned by incorporating suitable moiety into huperzine A. While the hydrolysis of the novel prodrug of the invention is carried out under a controlled manner, the appearance of huperzine A in the circulatory system and central nervous system is slower when compared to direct administration of huperzine A and thus avoids the over-exposure and fast elimination of the active pharmaceutical ingredient.

The following examples serve to illustrate the invention, but should not be construed as a limitation thereof.

EXAMPLE 1

O,N-Bis(phenoxycarbonyl)huperzine A

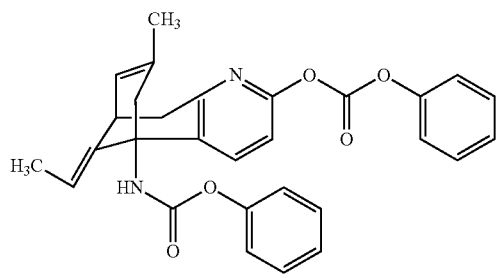

242 mg (1.00 mmol) (−)-huperzine A and 0.52 mL (3.00 mmol) N,N-diisopropylethylamine in 10 mL of dichloromethane were added 0.38 mL (3.00 mmol) phenyl chloroformate. The resulting mixture was stirred overnight at room temperature. The reaction mixture was worked up and the crude product was purified using silica gel chromatography with ethyl acetate-hexane (1:1) as an eluent to obtain the titled compound as a glassy material. $^1$H NMR (CDCl$_3$, 500 MHz) δ 7.91 (d, 1H, J=8 Hz, Pyridine-H), 7.59-6.88 (m, 10H, phenyl-H), 6.81 (d, 1H, J=8 Hz, Pyridine-H), 5.53 (q, 1H, J=6.5 Hz, vinyl-H), 5.43 (br d, 1H, J=5 Hz, vinyl-H), 3.68-1.51 (m, 11H, other H).

EXAMPLE 2

O,N-Bis(p-methoxyphenoxycarbonyl)huperzine A

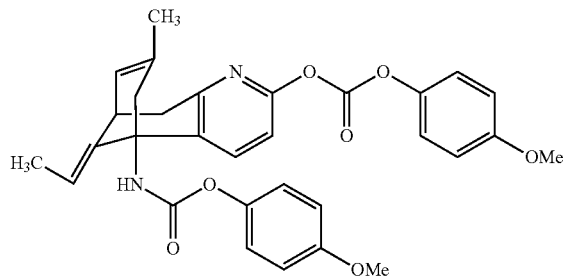

This compound was prepared according to the procedure of Example 1, with the exception that p-methoxyphenyl chloroformate was used in place of phenyl chloroformate. The structure of the purified compound was confirmed by NMR spectroscopy.

EXAMPLE 3

O,N-Bis(hexyloxycarbonyl)huperzine A

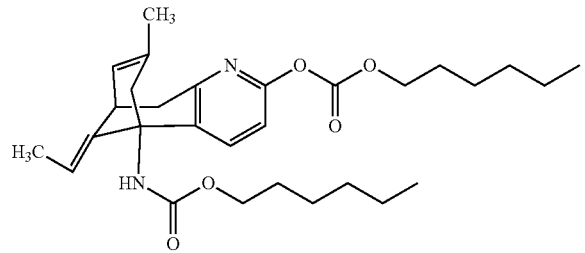

This compound was prepared according to the procedure of Example 1, above, with the exception that hexyl chloroformate was used in place of phenyl chloroformate. The structure of the purified compound was confirmed by NMR spectroscopy.

EXAMPLE 4

O,N-Bis(octyloxycarbonyl)huperzine A

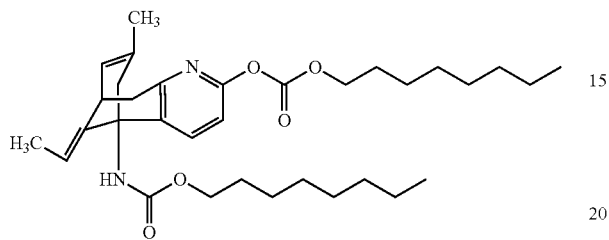

This compound was prepared according to the procedure of Example 1, above, with the exception that octyl chloroformate was used in place of phenyl chloroformate. The structure of the purified compound was confirmed by NMR spectroscopy.

EXAMPLE 5

O,N-Bis(2-ethylhexyloxycarbonyl)huperzine A

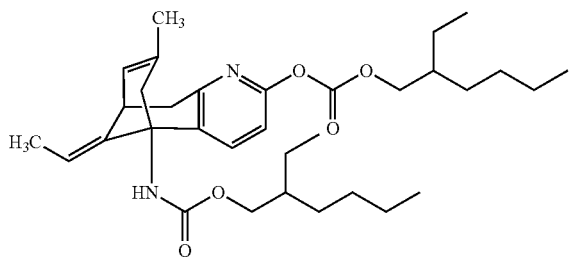

This compound was prepared according to the procedure of Example 1, above, with the exception that 2-ethylhexyl chloroformate was used in place of phenyl chloroformate. The structure of the purified compound was confirmed by NMR spectroscopy.

EXAMPLE 6

O,N-Bis(dodecyloxycarbonyl)huperzine A

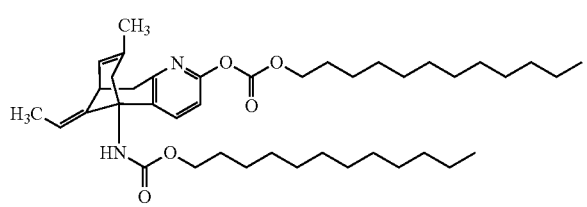

This compound was prepared according to the procedure of Example 1, above, with the exception that dodecyl chloroformate was used in place of phenyl chloroformate. The structure of the purified compound was confirmed by NMR spectroscopy.

EXAMPLE 7

O,N-Bis(cholesteryloxycarbonyl)huperzine A

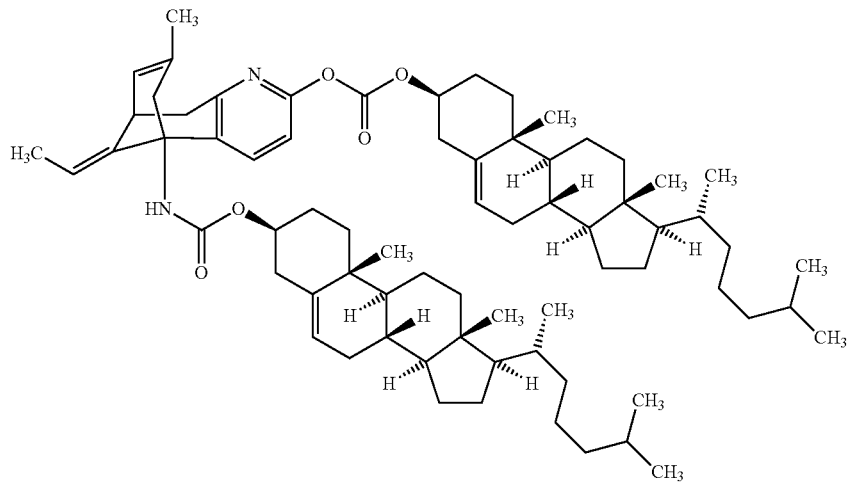

This compound was prepared according to the procedure of Example 1, above, with the exception that cholesteryl chloroformate was used in place of phenyl chloroformate. The structure of the purified compound was confirmed by NMR spectroscopy.

EXAMPLE 8

O,N-Bis(3-(ethoxycarbonyl)propionyl)huperzine A

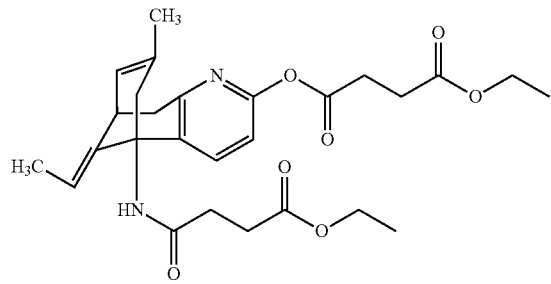

The titled compound was prepared according to the procedure of Example 1, above, with the exception that ethyl succinyl chloride was used in place of phenyl chloroformate. The structure of the purified compound was confirmed by NMR spectroscopy.

EXAMPLE 9

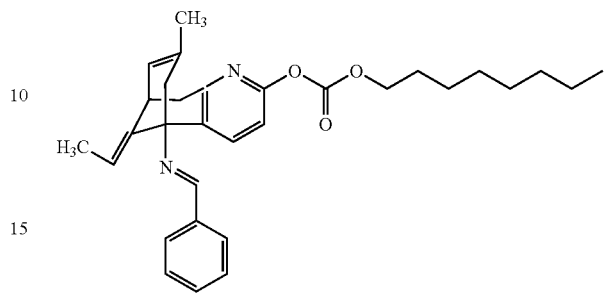

O-Octyloxycarbonyl-N-benzylidenehuperzine A

The starting material N-benzylidenehuperzine A was prepared according to the procedure described in U. S. Pat. No. RE38460. To a 10 mL THF solution, 303 mg (1.00 mmol) N-benzylidenehuperzine A was first treated with 123 mg (1.10 mmol) powder potassium t-butoxide and then 202 mg (1.05 mmol) octyl chloroformate in ice bath. The resulting mixture was stirred overnight and then worked up and the crude product was purified using silica gel chromatography with ethyl acetate:hexane (1:4) as an eluent to obtain the titled compound. $^1$H NMR (CDCl$_3$, 500 MHz) δ 8.47 (s, 1H, N=CH), 7.87 (d, 2H, J=8 Hz, phenyl-H), 7.47-7.42 (m, 3H, phenyl-H), 7.41 (d, 1H, J=8 Hz, pyridine-H), 6.90 (d, 1H, J=8 Hz, Pyridine-H), 5.52 (br d, 1H, J=5 Hz, vinyl-H), 5.24 (q, 1H, J=6.5 Hz, vinyl-H), 4.23 (t, H, J=7 Hz, OCOOCH$_2$), 3.78-0.87 (m, 26H, other H).

EXAMPLE 10

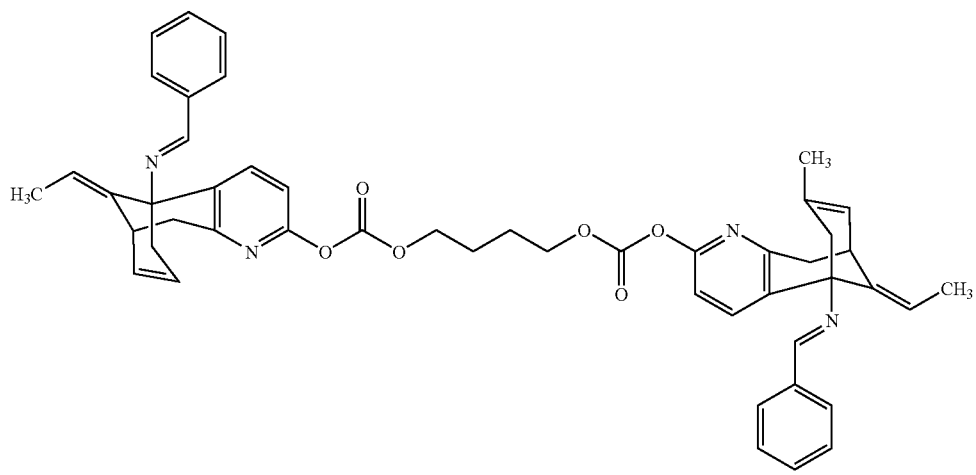

This compound was prepared according to the procedure of Example 9, above, with the exception that tetramethylene chloroformate was used in place of octyl chloroformate. The structure of the purified compound was confirmed by NMR spectroscopy.

EXAMPLE 11

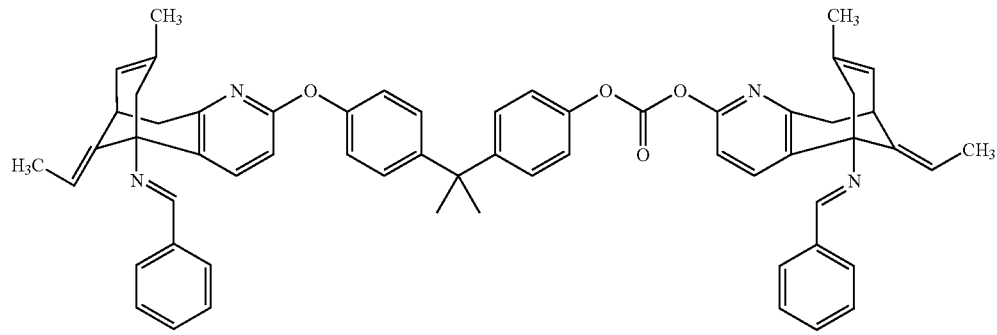

This compound was prepared according to the procedure of Example 9, above, with the exception that bisphenol A bis(chloroformate) was used in place of octyl chloroformate. The structure of the purified compound was confirmed by NMR spectroscopy.

EXAMPLE 12
O-(3-(Ethoxycarbonyl)propionyl)-N-biphenyl-4-ylmethylenehuperzine A

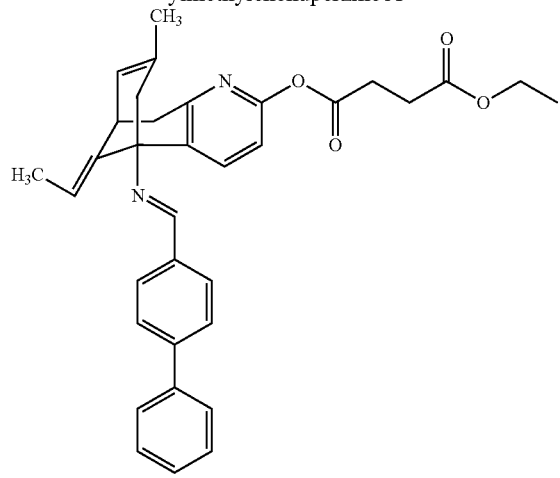

This compound was prepared according to the procedure of Example 9, above, with the exception that N-biphenyl-4-ylmethylenehuperzine A and ethyl succinyl chloride were used as starting materials. The structure of the purified compound was confirmed by NMR spectroscopy. $^1$H NMR (CDCl$_3$, 500 MHz) δ 8.48 (s, 1H, N=CH), 7.95-7.35 (m, 10H, Pyridine-H and biphenyl-H), 6.88 (d, 1H, J=8 Hz, Pyridine-H), 5.50 (br d, 1H, J=4 Hz, vinyl-H), 5.24 (q, 1H, J=6.5 Hz, vinyl-H), 4.14 (t, H, J=7 Hz, COOCH$_2$), 3.77-1.81 (m, 18H, other H).

EXAMPLE 13

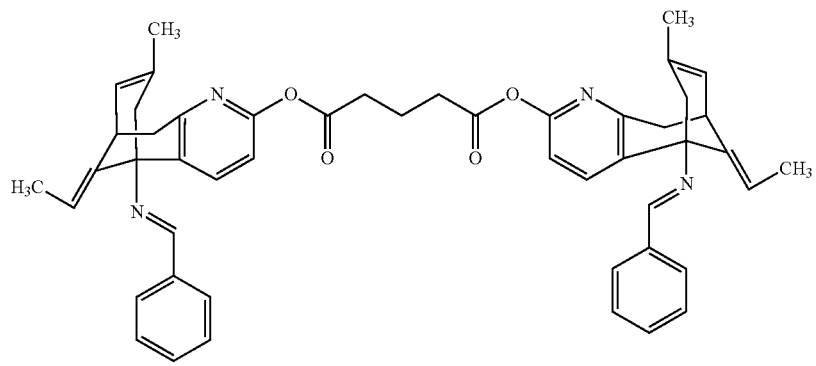

This compound was prepared according to the procedure of Example 9, above, with the exception that adipoyl dichloride was used in place of octyl chloroformate. The structure of the purified compound was confirmed by NMR spectroscopy.

EXAMPLE 14

O-Dimethylaminocarbonyl-N-benzylidenehuperzine A

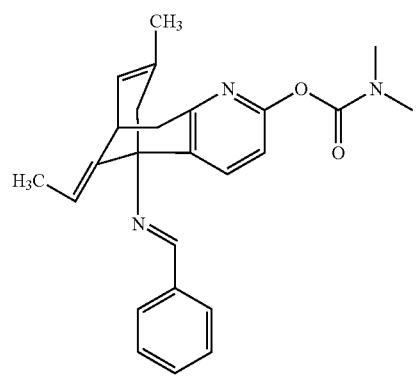

This compound was prepared according to the procedure of Example 9, above, with the exception that N,N-dimethylcarbamoyl chloride was used in place of octyl chloroformate. $^1$H NMR (CDCl$_3$, 500 MHz) δ 8.46 (s, 1H, N═CH), 7.87 (d, 2H, J=8 Hz, phenyl-H), 7.48-7.47 (m, 3H, phenyl-H), 7.39 (d, 1H, J=8 Hz, pyridine-H), 6.90 (d, 1H, J=8 Hz, Pyridine-H), 5.52 (br d, 1H, J=5 Hz, vinyl-H), 5.24 (q, 1H, J=6.5 Hz, vinyl-H), 3.77-1.61 (m, 17H, other H).

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A huperzine A compound selected from the group consisting of:

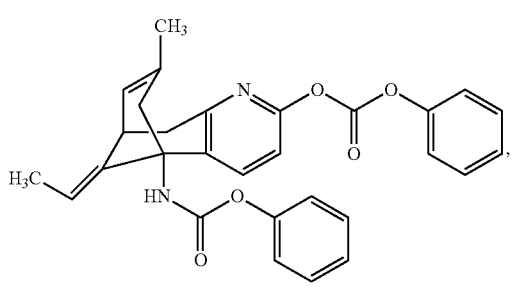

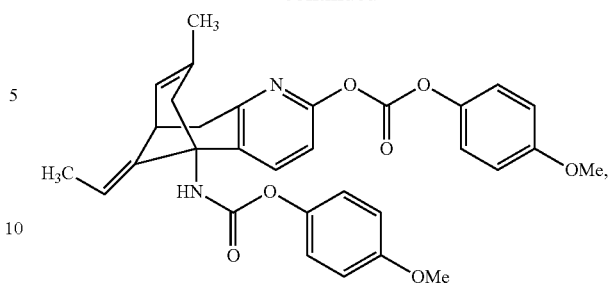

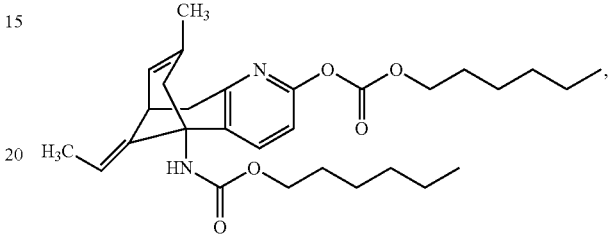

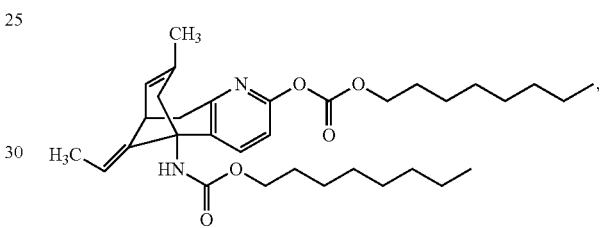

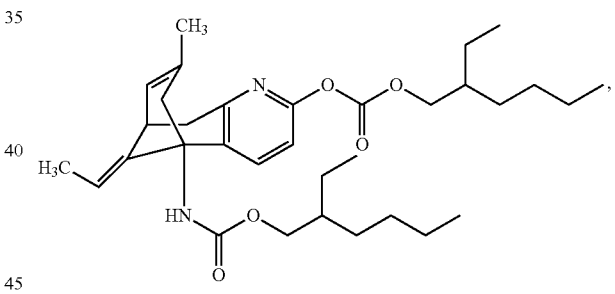

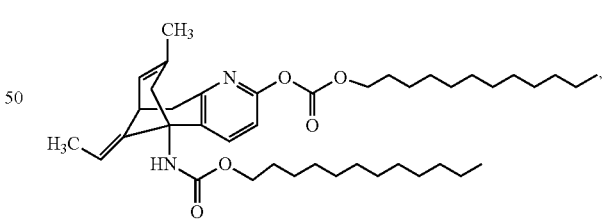

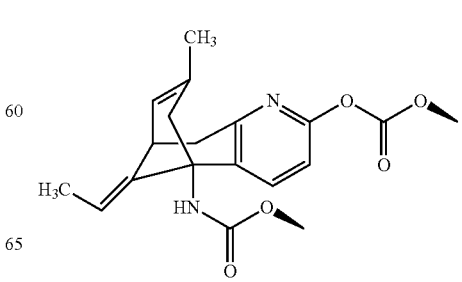

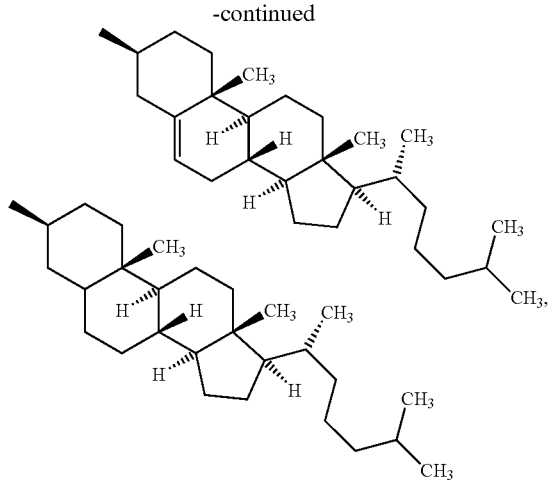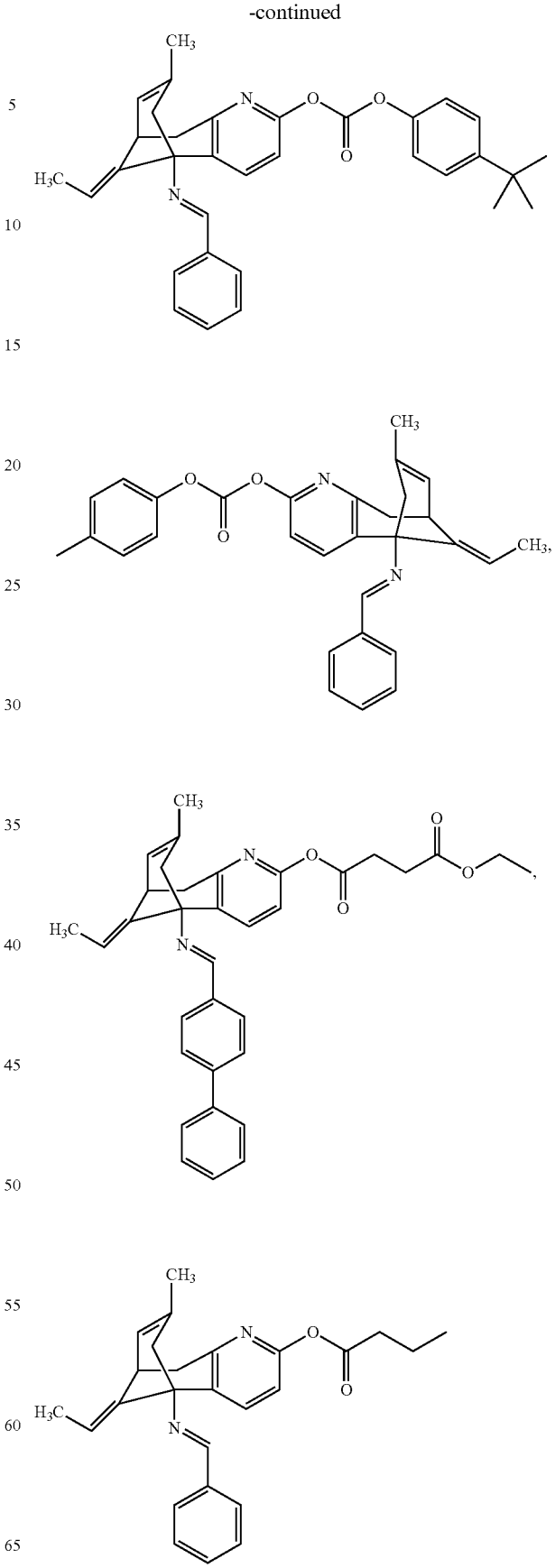

or pharmaceutically acceptable salts or complexes thereof.

2. A pharmaceutical composition, comprising:
a huperzine A compound according to claim 1 or pharmaceutically acceptable salts, or complexes thereof.

3. The huperzine A compound as claimed in claim 1, wherein the huperzine A compound is:

4. The huperzine A compound as claimed in claim 1, wherein the huperzine A compound is:

5. The huperzine A compound as claimed in claim 1, wherein the huperzine A compound is:

6. The huperzine A compound as claimed in claim 1, wherein the huperzine A compound is:

7. The huperzine A compound as claimed in claim 1, wherein the huperzine A compound is:

8. The huperzine A compound as claimed in claim 1, wherein the huperzine A compound is:
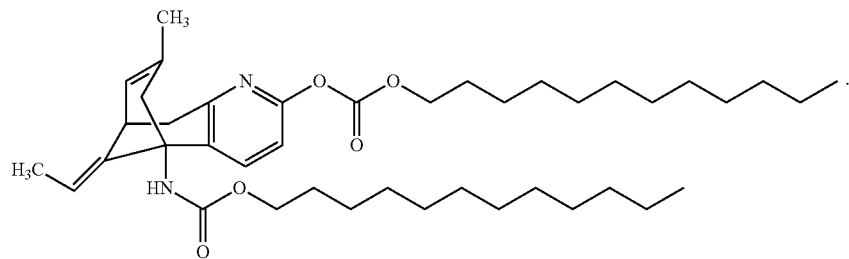
9. The huperzine A compound as claimed in claim 1, wherein the huperzine A compound is:
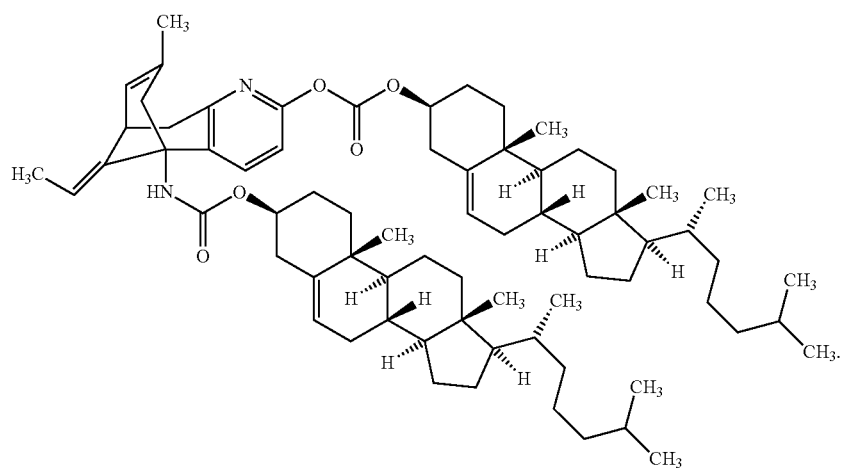
10. The huperzine A compound as claimed in claim 1, wherein the huperzine A compound is:
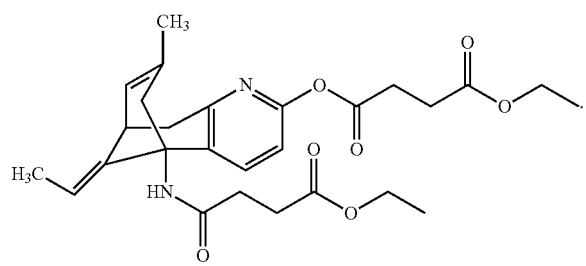
11. The huperzine A compound as claimed in claim 1, wherein the huperzine A compound is:
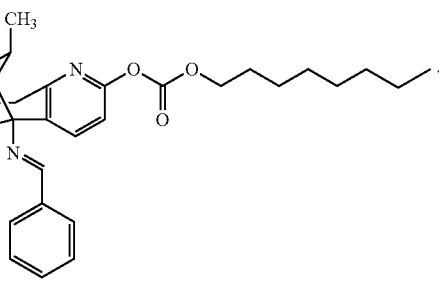

12. The huperzine A compound as claimed in claim 1, wherein the huperzine A compound is:
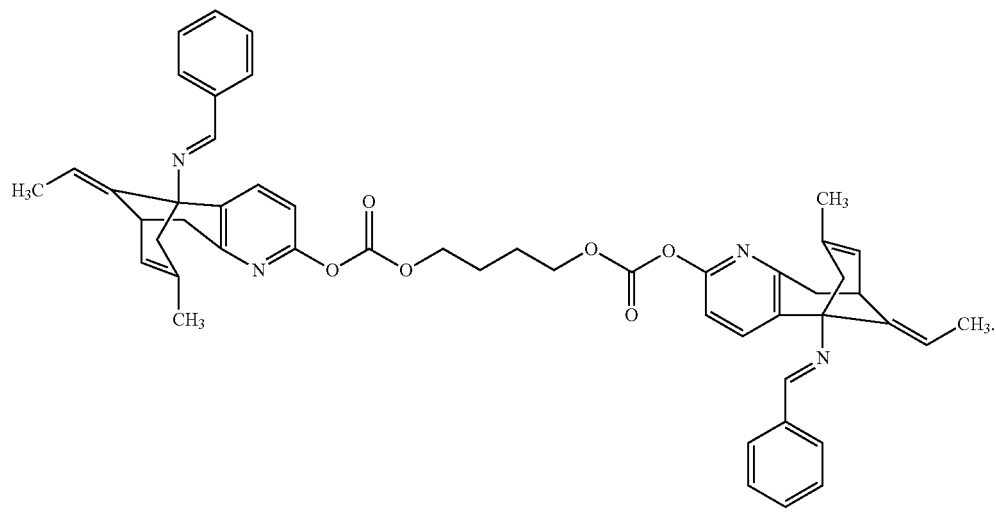
13. The huperzine A compound as claimed in claim 1, wherein the huperzine A compound is:
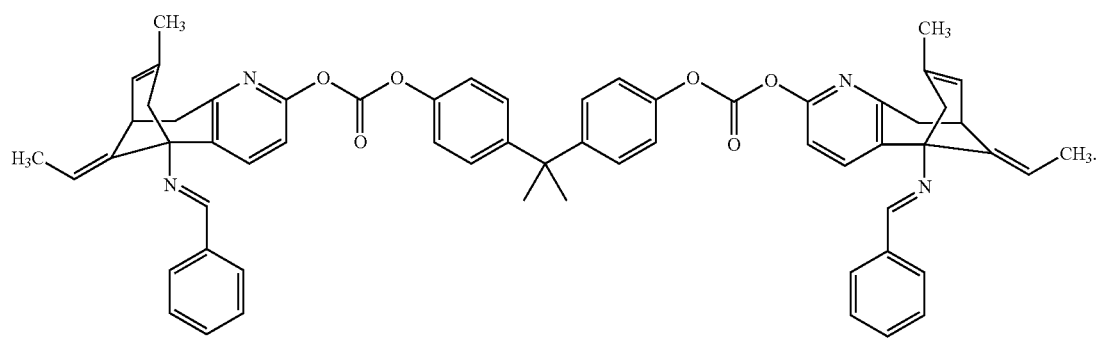
14. The huperzine A compound as claimed in claim 1, wherein the huperzine A compound is:
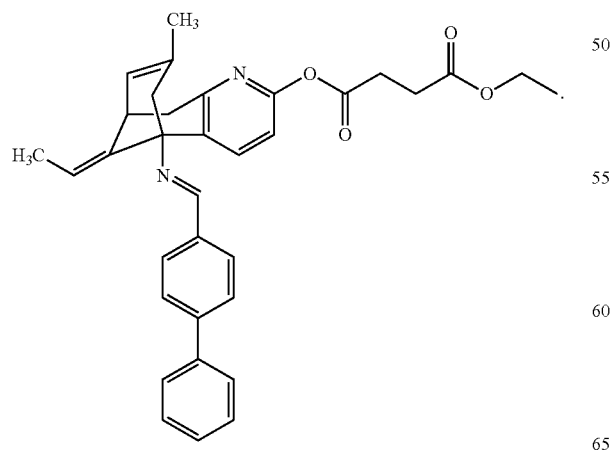

15. The huperzine A compound as claimed in claim 1, wherein the huperzine A compound is:
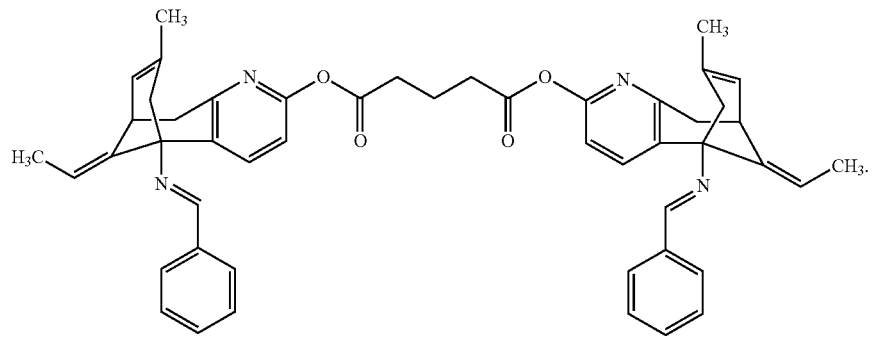
16. The huperzine A compound as claimed in claim 1, wherein the huperzine A compound is:
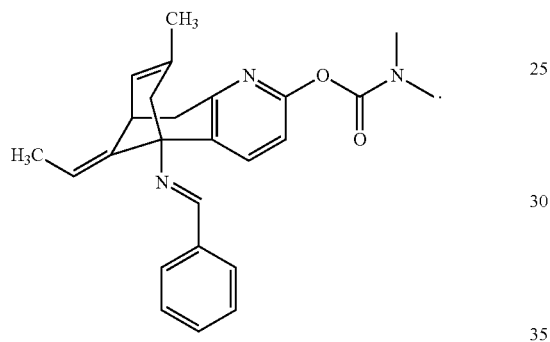
* * * * *